United States Patent [19]

Heavner et al.

[11] Patent Number: 5,298,490

[45] Date of Patent: Mar. 29, 1994

[54] TETRA AND PENTA-PEPTIDES USEFUL IN REGULATING THE IMMUNE SYSTEM

[75] Inventors: George Heavner, Flemington; Gideon Goldstein, Short Hills; Tapan Audhya, Bridgewater, all of N.J.

[73] Assignee: Immunobiology Research Institute, Inc., Annandale, N.J.

[21] Appl. No.: 462,743

[22] Filed: Jan. 9, 1990

Related U.S. Application Data

[63] Continuation-in-part of Ser. No. 268,692, Nov. 8, 1988, abandoned, which is a continuation-in-part of Ser. No. 196,138, May 19, 1988, abandoned.

[51] Int. Cl.$^5$ .................. A61K 37/02; C07K 5/10; C07K 7/06
[52] U.S. Cl. ........................... 514/17; 514/18; 530/330
[58] Field of Search .............. 530/330; 514/17, 18

[56] References Cited

U.S. PATENT DOCUMENTS

| | | | |
|---|---|---|---|
| 4,190,646 | 2/1980 | Goldstein et al. | 530/330 |
| 4,190,647 | 2/1980 | Goldstein et al. | 530/330 |
| 4,261,886 | 4/1981 | Goldstein et al. | 530/330 |
| 4,309,340 | 1/1982 | Sarantakis et al. | 530/330 |
| 4,361,673 | 11/1982 | McGregor | 530/330 |
| 4,420,424 | 12/1982 | Geiger et al. | 530/330 |
| 4,428,938 | 1/1984 | Kisfaludy et al. | 530/330 |
| 4,505,853 | 3/1985 | Goldstein et al. | 530/330 |
| 4,547,489 | 10/1985 | Goldstein et al. | 530/330 |
| 4,614,517 | 9/1986 | Ruoslahti et al. | 530/330 |
| 4,629,723 | 12/1986 | Goldstein et al. | 530/330 |
| 4,742,048 | 5/1988 | Bouchaudon et al. | 530/330 |

FOREIGN PATENT DOCUMENTS

| | | |
|---|---|---|
| 0018182 | 10/1980 | European Pat. Off. . |
| 25897 | 4/1981 | European Pat. Off. . |
| 37246 | 10/1981 | European Pat. Off. . |
| 0042291 | 12/1981 | European Pat. Off. . |
| 0067425 | 12/1982 | European Pat. Off. . |
| 0025897 | 6/1983 | European Pat. Off. . |
| 80194 | 6/1983 | European Pat. Off. . |
| 164654 | 5/1985 | European Pat. Off. . |
| 282891 | 9/1988 | European Pat. Off. . |
| 0352560 | 1/1990 | European Pat. Off. . |
| 3401545A1 | 2/1985 | Fed. Rep. of Germany . |
| 3421614 | 12/1985 | Fed. Rep. of Germany . |
| 1237918 | 7/1971 | United Kingdom . |

OTHER PUBLICATIONS

Kisfaludy et al, Hoppe-Seyler's Z. Physiol. Chem., 364:933-940 (1983).
G. Goldstein, Nature (London) 247:11-14 (1974).
R. S. Basch et al Proc. Natl. Acad. Sci. USA., 71:1474-1478 (1974).
M. P. Scheid et al, J. Exp. Med., 147:1727-1743 (1978) [Scheid I].
M. P. Scheid et al, Science, 190:1211-1213 [Scheid II].
G. E. Ranges et al, J. Exp. Med., 156:1057-1064 (1982).
K. Venkatasubramanian et al, Proc. Nat. Acad. Sci. USA., 83:3171-3174 (1986).
M. G. Malaise et al in "Immunoregulatory UCLA Symposium on Molecular and Cellular Biology", eds. G. Goldstein et al (Liss, New York) (1986) [Malaise I].
G. H. Sunshine et al, J. Immunol., 120:1594-1599 (1978).
G. A. Heavner et al, Peptides, 7:1015 (1986).
T. Abiko et al, Chemo. Pharm. Bull., 27(9):2233-2237 (1979) [Abiko I].
T. Abiko et al, Chem. Pharm. Bull., 28(8):2507-2511 (1980) [Abiko II].
T. Abiko et al, Chem. Pharm. Bull., 29(8):2322-2329 (1981) [Abiko III].

(List continued on next page.)

Primary Examiner—Lester L. Lee
Attorney, Agent, or Firm—Howson and Howson

[57] ABSTRACT

Tetrapeptides and pentapeptides are disclosed which are capable of regulating the function of cells of the mammalian immune system. Also provided are pharmaceutical compositions containing the peptides and methods of use thereof.

30 Claims, 6 Drawing Sheets

OTHER PUBLICATIONS

T. Abiko, Chem. Pharm. Bull., 29(11):3320–3325 (1981) [Abiko IV].
T. Abiko et al, J. A-pl. Biochem., 7:408–422 (1985) [Abiko V].
K. Kisfaludy et al, Ann. Immunol. Hung., 25:189–193 (1985) [Kisfaludy II].
E. Rentz,. Arch. Geschwulstforsch, 54:113–118 (1984).
G. I. Chipens et al, Bioorganicheskaya Khimiya, 11(4):437–446 (1985).
Kessler et al, Liebigs. Ann. Chem., (1986) pp. 869–931 and German Application No. DE 3401545 (1985).
E. Ivan et al, Arch. Toxical., Suppl. 8, pp. 495–498 (1985).
Chu et al, Journal of Investigative Dermatology, 81:194–197 (1983).
Audhya et al, Int. J. Peptide Protein Res., 22:568–572 (1983).
Malaise et al, The Lancet, 832–836 (1985).
Audhya et al. Biochem., 20:6195–6200 (1980).

TETRA AND PENTA-PEPTIDES USEFUL IN REGULATING THE IMMUNE SYSTEM

This is a continuation-in-part application of pending U.S. patent application Ser. No. 07/268,692, filed Nov. 8, 1988 and now abandoned which was a continuation-in-part application of U.S. patent application Ser. No. 07/196,138 filed May 19, 1988 and now abandoned.

The present invention relates generally to synthetic peptides capable of stimulating the mammalian immune system, particularly, in stimulating T helper cells and in stimulating T suppressor cells, or in the repair of the suppressor functions in certain disease states. The peptides of the present invention are tetrapeptides and pentapeptides based on the molecules thymopoietin and thysplenin.

BACKGROUND OF THE INVENTION

The immunomodulatory proteins, thymopoietin and thysplenin (formerly referred to as "splenin"), have been isolated from bovine and human thymus and spleen, respectively. Additionally, small peptides have been chemically synthesized which mimic the biological activity of thymopoietin and have been further modified to be provided with additional attributes such as resistance to enzymatic action. See, e.g. U.S. Pat. No. 4,505,853.

A large body of articles and patents have now been published relating to such proteins and synthesized peptides. U.S. Pat. No. 4,190,646 discloses the pentapeptide thymopentin which is the active site of thymopoietin and has the sequence Arg-Lys-Asp-Val-Tyr, as well as peptide compositions in which various groups are substituted onto the amino and/or carboxy termini of this pentapeptide. Both thymopoietin and thymopentin induce biological changes in two human T cell lines, CEM and MOLT-4, thereby indicating a role in stimulating biological activities of T cells. No analogs of thymopentin shorter than pentapeptides (5 amino acids in sequence) were found to be active on CEM cells.

Applicants' copending U.S. patent application Ser. No. 53,186 discloses a 48 amino acid immuno-modulatory protein, splenin, (hereafter referred to as "thysplenin") isolated from human spleen having the amino acid sequence -Gly-Leu-Pro-Lys-Glu-Val-Pro-Ala-Val-Leu-Thr-Lys-Gln-Lys-Leu-Lys-Ser-Glu-Leu-Val-Ala-Asn-Asn-Val-Thr-Leu-Pro-Ala-Gly-Glu-Met-Arg-Lys-Ala-Val-Tyr-Val-Glu-Leu-Tyr-Leu-Gln-Leu-Tyr-Leu-Gln-Ser-Leu-Thr-Ala-Glu-His-. Bovine thysplenin stimulates helper T cell activity in vivo in mice. Human thysplenin is thus expected to exhibit analogous biological activity in humans. Human thysplenin was described in the above-identified application as inducing elevation of intracellular cGMP in the human T cell line MOLT-4. The active site of bovine thysplenin, called SP-5, spans amino acid residues 32–36 thereof and has the sequence Arg-Lys-Glu-Val-Tyr. In application Ser. No. 56,186 the active site of the human sequence was disclosed as Arg-Lys-Ala-Val-Tyr. This application which issued as U.S. Pat. No. 4,923,964 (see also European Patent Application 292,302, published Nov. 23, 1988) is incorporated herein by reference.

Thysplenin, unlike thymopoietin, does not produce changes in biological activity of CEM cells. Thus thysplenin is implicated in the stimulation of T cell helper activity, not T cell suppressor activity. See also, for example, Goldstein, G. *Nature* (London) 247: 11–14 (1974); Basch, R. S. and Goldstein, G., *Proc. Natl. Acad. Sci U.S.A.*, 71: 1474–1478 (1974); Scheid, M. P. et al *J. Exp. Med.*. 147: 1727–1743 (1978); Scheid, M. P. et al *Science*, 190: 1211–1213 (1975); Ranges, G. E. et al, *J. Exp. Med.*, 156: 1057–1064 (1982); T. Audhya et al., *Biochem*, 20: 6195–6200 (1981); Venkatasubramanian, K., et al, *Proc. Natl. Acad. Sci. U.S.A.*, 83: 3171–3174 (1986); Malaise M. G. et al, in "Immunoregulatory UCLA Symposium on Molecular and Cellular Biology", eds. Goldstein, G., et al (Liss, New York) (1986); Sunshine, G. H. et al, *J. Immunol.*, 120: 1594–1599 (1978) and E. Rentz et al, *Arch. Geschwulstforsch*, 54(2): 113–118 (1948). See also U.S. Pat. Nos. 4,190,646; 4,261,886; 4,361,673; 4,420,424; and 4,629,723. Reference is made to the above-described patents, applications and articles for a discussion of other background material and the biological processes involved in the present invention.

U.S. Pat. No. 4,428,938 by Kisfaludy et al, issued Jan. 31, 1984, discloses certain peptides affecting immune regulation. Among such peptides are the following tetrapeptides:

Arg-Lys-Asp-Val
Arg-Lys-Asn-Val
Arg-Lys-Ala-Val
Arg-Lys-Asp-Ala
Arg-Lys-Asp-Ile
Arg-Lys-Glu-Val
Glp-Arg-Lys-Asp

The '938 patent generally includes the salts, amides, lower alkyl esters and protected derivatives of these sequences, as well as methods for using these sequences to treat immunological disorders due to thymic deficiencies. In this patent the peptides were tested for activity in an in vitro E rosette assay.

The same researchers reported such tetrapeptides in Kisfaludy et al, *Hoppe-Seyler's Z. Physiol. Chem.* B.D. 364, S. 933–940 (1983). In that paper it was reported that the sequence Arg-Lys-Glu-Val was a highly active analog in an in vitro E rosette test, and that the sequences Arg-Ala-Asp-Val and Arg-Lys-Ala-Val have drastically reduced activity.

There remains a need in the art for additional peptides which are useful in stimulating the immune system of humans for a variety of disease states to which deficiencies in T cell number or malfunctioning T cells contribute.

SUMMARY OF THE INVENTION

The present invention describes a series of thysplenin peptide analogs capable of regulating the function of cells of the immune system.

As one aspect, the present invention relates to novel tetrapeptides having the following formula:

(I) R-Arg-X-Y-Z-R$^1$ or a pharmaceutically acceptable acid- or base-addition salt thereof, wherein
  R is H, lower alkyl, acetyl, formyl, lower alkanoyl;
  X is Pro, dehydro-Pro, hydroxy-Pro, D-Lys, α-methylalanine (Aib), or Lys;
  Y is a D or L amino acid selected from Ala, Asp, Glu, Gln, Asn, beta Asp, Val, Leu, or Ile;
  Z is Gly or a D or L amino acid selected from Val, Ala, Leu or Ile; R$^1$ is NR$^2$R$^3$, wherein R$^2$ and R$^3$ are H or a straight chain or branched alkyl or alkenyl having 1 to 6 carbon atoms, optionally substituted with an aryl group or aryl substituted with either a halogen or a straight chain or branched alkyl or alkenyl having 1 to 6 carbon atoms or wherein $R^2$ and $R^3$ together comprise a cyclic methylene group of 3 to 7 carbon atoms, provided that when X is Lys, and Z is Val, Y is other than Asp, Asn, Ala, Asu, or Glu; and when X is Lys, Y is other than Asp; and when X is Ala and Z is Val, Y is other than Asp.

In another aspect, the present invention relates to novel pentapeptides having the following formula:

(II) $R^4$-Arg-X'-Ala-Y'-Z'-$R^5$ or a pharmaceutically acceptable acid- or base-addition salt thereof, wherein $R^4$ is H, lower alkyl, acetyl, formyl, lower alkanoyl, or des-amino;

X' is Pro, dehydro-Pro, hydroxy-Pro, D-Lys, Aib, or Lys;

Y' is a D or L amino acid selected from Val, Ile, Leu, Lys, Ala, Asp, Glu, Gln;

Z' is a D or L amino acid selected from Tyr, Val, Leu, His, Ala, Phe or Trp; and $R^5$ is OH or $NR^6R^7$, wherein $R^6$ and $R^7$ are H or a straight chain or branched alkyl or alkenyl having 1 to 6 carbon atoms, optionally substituted with an aryl group or aryl substituted with either a halogen or a straight chain or branched alkyl or alkenyl having 1 to 6 carbon atoms or wherein $R^6$ and $R^7$ together comprise a cyclic methylene group of 3 to 7 carbon atoms.

Preferred peptides of these formulae characterized by enhanced resistance to attack by endo- and exopeptidases and trypsin-like enzymes in the digestive tract and in serum. This enhanced resistance to enzymatic digestion in the intestinal tract makes such peptides particularly desirable for oral administration. Such desirable tetrapeptides are characterized by the presence of an amino terminal acetyl a carboxy terminal substituted amide and having the second amino acid of the peptide being proline or AIB. Such desirable pentapeptides are characterized by the presence of an amino terminal acetyl, a carboxy terminal —OH or substituted amide and having the second amino acid of the peptide being proline or AIB.

These peptides and compositions containing these peptides surprisingly demonstrate a variety of regulatory effects on the mammalian immune system. The peptides retain the biological activity of human thysplenin. These peptides are also characterized by the ability to inhibit tumor or viral growth. Additionally the peptides of this invention have been shown to stimulate or repair suppressor function. Thus, these peptides offer significant advantages in the treatment of immune defects.

Yet a further aspect of this invention includes therapeutic compositions containing these peptides and methods for use of these peptides in treating a variety of conditions or diseases requiring immune regulation.

Other aspects and advantages of the present invention are disclosed in the following detailed description containing examples of presently preferred embodiments.

DETAILED DESCRIPTION OF THE INVENTION

The present invention provides peptides capable of regulating and effecting the mammalian immune system. These peptides are capable of inducing biological activity in the MOLT-4 T cell line. Unlike the thymopentin analogs previously reported, peptides smaller than five amino acids in length and related to thysplenin are active in inducing cGMP elevations in MOLT-4 cells, associated with T cell helper activity. The pentapeptide analogs of thysplenin described herein also display this activity. These peptides have also shown an effect on the immune system in stimulating or repairing deficient T cell suppressor function in autoimmune states. These peptides have also demonstrated an effect in activating T cell helper cells to combat the growth of tumor cells and the spread of viral infection.

The present invention provides a series of tetrapeptides having the formula:

(I) R-Arg-X-Y-Z-$R^1$ or a pharmaceutically acceptable acid or base addition salt thereof, wherein, R, X, Y, Z and $R^1$ are as defined above and provided that when X is Lys, and Z is Val, Y is other than Asp, Asn, Ala, Asu, or Glu, and when X is Lys, Y is other than Asp; and when X is Ala and Z is Val, Y is other than Asp.

The invention also provides a series of pentapeptides having the formula:

(II) $R^4$-Arg-X'-Ala-Y'-Z'-$R^5$ or a pharmaceutically acceptable acid or base addition salt thereof, wherein $R^4$, X', Y', Z' and $R^5$ are as defined above. These peptides are also characterized by the ability to induce activity in MOLT-4 cells. Preferred peptides according to this formula also include those where $R^4$ is acetyl, X is Pro or AIB, and $R^5$ is an alcohol or substituted amide.

As used herein, the term "lower alkyl" includes branched and straight-chain saturated hydrocarbons having from one to six carbon atoms, such as methyl, ethyl, propyl, isopropyl, pentyl, hexyl, and the like, while the term "lower alkanoyl" means lower alkyl Throughout this disclosure, the amino acid components of the peptides and certain materials used in their preparation are identified by abbreviations for convenience. Most of the three letter abbreviations for amino acids are well known. Several less known abbreviations are Asu, for amino-succinimidyl and Glp for pyroglutamyl (also p-Glu). Unless otherwise indicated all amino acids are the L-isomeric configuration. Where the D-isomeric configuration is desired, it will be so indicated.

Certain preferred tetrapeptides of the present invention are those of the above formula I wherein X is Pro or AIB. More preferred peptides are those of formula I wherein X is Pro, Y is Val and Z is Ala or wherein X is Pro, Y is Ala, and Z is Val.

In a preferred embodiment, peptides of the present invention are particularly suitable for oral administration and capable of resisting degradation by enzymes present in the intestinal tract. Such tetrapeptides are characterized by the above formula where R is acetyl, X is Pro, and $R^1$ is $NR^2R^3$. Such pentapeptides are characterized by the above formula where R is acetyl, X is Pro, and $R^5$ is OH or $NR^6R^7$. In these preferable peptides only one R substituent is H, while the other is an alkyl or alkenyl as described above. Alternatively, both R substituents on the nitrogen may be other than H, as described above.

Thus, in a particularly preferred embodiment, the invention includes the peptide Acetyl-Arg-Pro-Val-Ala-NH$_2$. In another particularly preferred embodiment the invention includes the peptide Acetyl-Arg-Pro-Val-Ala-NH(CH$_3$). Another preferred peptide is Acetyl-Arg-Pro-Glu-Val-NH$_2$. Still a further preferred peptide is Acetyl-Arg-Pro-Glu-Val-NH(CH$_3$). The peptide Acetyl-Arg-Pro-Asp-Val-NH(CH$_3$) is also preferred. Other tetrapeptides bearing an amino terminal acetyl and/or a carboxy terminal substituted amide retain enhanced resistance to degradation of these peptides.

Several other preferred tetrapeptides are the following peptides:

Arg-Pro-Asp-Val
Arg-Pro-Asp-Val-NH$_2$
Formyl-Arg-Pro-Asp-Val
Acetyl-Arg-Pro-Asp-Val
Acetyl-Arg-Pro-Asp-Val-NH(CH$_3$)
Acetyl-Arg-Pro-Asp-Val-NH$_2$
Acetyl-Arg-Pro-Ala-Val-NH$_2$
Acetyl-Arg-Pro-D-beta-Asp-Val-NH$_2$
Acetyl-Arg-Pro-Glu-Val-NH$_2$
Acetyl-Arg-Pro-Glu-Val
Acetyl-Arg-Aib-Ala-Val-NH$_2$
Acetyl-Arg-Aib-Glu-Val-NH$_2$ and
Acetyl-Arg-Pro-beta-Asp-Gly-NH$_2$.

Certain preferred pentapeptides of the present invention are those of formula wherein X' is Pro or Aib. More preferred peptides are those of the formula above wherein X' is Pro, Y' is Val, and Z' is Tyr. Pentapeptides of this invention having an amino terminal acetyl, a carboxy terminal —OH or substituted amide, and X being Pro or AIB are expected to demonstrate enhanced resistance to enzymatic degradation.

Preferred pentapeptides include the following peptides:

Arg-Pro-Ala-Val-Tyr
Arg-Pro-Ala-Val-Tyr-NH$_2$
Acetyl-Arg-Lys-Ala-Val-Tyr-NH$_2$ Acids which are able to form salts with these peptides include, but are not limited to, inorganic acids, such as hydrochloric acid, hydrobromic acid, perchloric acid, nitric acid, thiocyanic acid, sulfuric acid, phosphoric acid, and the like. Organic acids may also be employed to form the salts of the invention, e.g., formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, sulfanilic acid, and the like.

A nonexclusive list of bases which are able to form salts with those peptides having acidic moieties includes inorganic bases, such as sodium hydroxide, ammonium hydroxide, potassium hydroxide, and the like. Organic bases for such use include, without limitation thereto, mono-, di-, and tri-alkyl and aryl amines (e.g., triethylamine, diisopropylamine, methylamine, dimethylamine) and optionally substituted ethanolamines (e.g., ethanolamine, diethanolamine).

The peptides of this invention may generally be prepared following known techniques. Conveniently, synthetic production of the polypeptide of the invention may be according to the solid phase synthetic method described by Merrifield in *J.A.C.S.* 85: 2149–2154 (1963). This technique is well understood and is a common method for preparation of peptides. The solid phase method of synthesis involves the stepwise addition of protected amino acids to a growing peptide chain which is bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond. Succeeding protected amino acids are added, one at a time, or in blocks, in a stepwise manner until the desired sequence is assembled. Finally, the protected peptide is removed from the solid resin support and the protecting groups are cleaved off.

The amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate, and polystyrene. Appropriate protective groups usable in such synthesis include t-butyloxycarbonyl (BOC), benzyl (BZL), t-amyloxycarbonyl (AOC), tosyl (TOS), o-bromophenylmethoxycarbonyl (BrZ), 2,6-dichlorobenzyl (BZLCl$_2$), and phenylmethoxycarbonyl (Z or CBZ). Additional protective groups are identified in the above text, as well as in J. F. W. McOmie, "Protective Groups in Organic Chemistry", Plenum Press, New York, 1973. Both of these books are incorporated herein by reference.

The general procedure of preparation of the peptides of this invention involves initially attaching the protected C-terminal amino acid to the resin. After attachment the resin is filtered, washed and the protecting group (desirably t-butyloxycarbonyl) on the alpha amino group of the C-terminal amino acid is removed. The removal of this protecting group must take place, of course, without breaking the bond between that amino acid and the resin. To the resulting resin peptide is then coupled the penultimate C-terminal protected amino acid. This coupling takes place by the formation of an amide bond between the free carboxy group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Alternative techniques for peptide synthesis are described in "Peptide Synthesis" by Bodanszky, et al, second edition, John Wiley and Sons, 1976. For example, the peptides of the invention may also be synthesized using standard solution peptide synthesis methodologies, involving either stepwise or block coupling of amino acids or peptide fragments using chemical or enzymatic methods of amide bond formation. These solution synthesis methods are well known in the art.

The peptides of this invention may also be produced by other techniques known to those of skill in the art, for example, genetic engineering techniques. See, e.g., T. Maniatis et al, in *Molecular Cloning, a Laboratory Manual,* Cold Spring Harbor Laboratory, Cold Spring Harbor, New York (1982).

The peptides of this invention have been found to exhibit a variety of regulatory effects on the mammalian immune systems. For example, the peptides demonstrate a T cell helper stimulating biological activity similar to human thysplenin as disclosed in the above referenced U.S. patent application and articles. This biological activity was initially evidenced by an in vitro assay measuring the induction of cyclic GMP production in the human T cell line MOLT-4 in comparison with human thysplenin and human thymopentin. The induction of c-GMP production by a peptide of the present invention in this assay indicates the ability of that peptide to bind to the human thysplenin receptor site on the cell and induce human thysplenin-like biological activity.

Prior to the testing of the peptides of the present invention, it was not expected that tetra- or pentapeptide analogs of human thysplenin could be prepared having the same biological specificity because Arg-Lys-Ala-Val-Tyr, which is the human analog of the bovine pentapeptide SP-5 (Arg-Lys-Glu-Val-Tyr), is inactive on MOLT-4 cells. Thus, the discovery of pentapeptide and tetrapeptide analogs of human thysplenin that demonstrated the same biological activity as the intact human thysplenin molecule was unexpected.

The T-cell helper stimulatory activity of the peptides is also illustrated below in the in vivo assay of Example 9, demonstrating inhibition of tumor growth in animals treated with a peptide of this invention vs. a placebo. The T-cell helper activity is also evidenced by the in vivo assay of Example 10, demonstrating an inhibition of viral infection in animals treated with a peptide of this invention vs. a placebo.

An even more unexpected therapeutic effect on the mammalian immune system mediated by a peptide of this invention is in stimulating or repairing deficient T cell suppressor function. This therapeutic function is of great value in the treatment of auto-immune diseases, normally treated with steroids, which are toxic poisons and block the output of the immune system. The peptides of the present invention have demonstrated in the in vivo assay of Example 11 an ability to repair or stimulate the suppressor function in subjects having an autoimmune disease. This function should also be useful in stimulating the immune system for allergy treatments.

Many of the subject tetrapeptides and pentapeptides offer a further significant advantage over human thysplenin. Many peptides of the present invention are characterized by resistance to enzymatic degradation by either digestive or serum enzymes. Thus they demonstrate a prolonged half-life in vivo when administered by injection in a biological subject. Another advantage of many of these peptides is their capacity to be administered orally. Human thysplenin itself is too large a molecule to be effectively administered orally and would be digested in the gastointestinal tract.

Because of the immunomodulatory characteristics of the subject peptides, they are therapeutically useful in the treatment of humans, and possibly animals, since they have the capability of inducing the differentiation and maturation of T cells (both helper and suppressor) which are capable of involvement in the immune response of the body. As a result, the subject peptides are considered to have multiple therapeutic uses.

The peptides of this invention are considered useful in assisting the collective immunity of the body, in that they will increase or assist in therapeutic stimulation of cellular immunity. They are thereby useful in the treatment of diseases involving chronic infection, such as fungal or mycoplasma infections, tuberculosis, leprosy, acute and chronic viral infections and the like.

The subject peptides or pharmaceutical compositions containing the peptides or their acid or basic salts are generally considered to be useful in any area in which cellular immunity is an issue and particularly where there are deficiencies in immunity. Thus, where there is an excess of antibody production due to unbalanced T cells, the subject peptides can correct this condition by stimulating T cell function. Additionally the peptides are capable of repairing or stimulating deficient T cell suppressor function. Thus, they are expected to be of therapeutic use in autoimmune diseases in which damaging antibodies are produced, such as systemic lupus erythematosus, rheumatoid arthritis, or a variety of allergies.

In their broadest application, the subject peptides or pharmaceutical compounds containing same are useful for regulating the immune system of a subject, human or animal, in need of such regulation. As used herein, the term "regulate" means that the subject compounds cause the immune system to return from an abnormal, diseased state to a normal, balanced state. While this regulation may well find great application in the correction of immunological deficiencies (e.g., DiGeorge syndrome), it is also applicable to correct conditions of excess immunological activity (e.g., autoimmune diseases). Thus, the peptides have also shown utility in the reduction of tumor growth, and may be helpful in therapeutic treatment of certain cancers characterized by solid tumors.

The present invention therefore includes methods for regulating the immune system of a human or animal in need of such regulation which comprises administering to said human or animal at least one of the peptides in an amount effective in regulating the immune system, as well as pharmaceutical compositions for practicing these methods.

The invention also provides a method for treatment of conditions resulting from relative or absolute deficiencies of the immune system of a subject, which comprises administering to said subject a therapeutically-effective amount of at least one of the peptides of this invention.

As used herein, the term "therapeutically-effective amount" means an amount which is effective to treat the conditions referred to above. The invention also provides a method for inducing the differentiation and maturation of T cells which comprises administering to the subject an effective inducing amount of at least one of the peptides of the invention.

The invention further provides pharmaceutical compositions for practicing those methods. To prepare the pharmaceutical compositions of the present invention, a peptide of this invention is combined as the active ingredient in intimate admixture with a pharmaceutical carrier according to conventional pharmaceutical compounding techniques. This carrier may take a wide variety of forms depending on the form of preparation desired for administration, e.g., oral, sublingual, rectal, nasal, or parenteral.

In preparing the compositions in the preferred oral dosage form, any of the usual pharmaceutical media may be employed. For oral liquid preparations (e.g., suspensions, elixirs, and solutions), media containing, for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For parenteral products, the carrier will usually comprise sterile water, although other ingredients, e.g., to aid solubility or for preservation purposes may be included. Injectable suspensions may also be prepared, in which case appropriate liquid carriers, suspending agents, and the like may be employed.

A tetrapeptide or pentapeptide of the present invention is generally active when administered in amounts above about 0.01 μg/kg of body weight and preferably from about 0.001 to about 10 mg/kg body weight. Generally, the same range of dosage amounts may be used in treatment of the diseases or conditions mentioned where immunodeficiency is to be treated. The following examples are presented to illustrate the invention without specifically limiting the invention thereto. In the examples and throughout the specification, parts are by weight unless otherwise indicated. The examples employ the following abbreviations: TFA for trifluoroacetic acid; HOAc for acetic acid; $CH_2Cl_2$ for methylene chloride; $CH_2CN$ for acetonitrile; DMF for dimethyl formamide; $NH_4OAc$ for ammonium acetate; $NH_4OH$ for ammonium hydroxide; n-PrOH for n-propanol; n-BuOH for n-butanol; pyr for pyridine; DCC for dicyclohexylcarbodiimide; HOBt for 1-hydroxybenzotriazole; DMAP for dimethylaminopyridine; HF for hydrogen fluoride TCA for trichloroacetic acid; BHA for benzhydrylamine; and MeOH for methanol.

EXAMPLE 1

Synthesis of a Tetrapeptide:
Acetyl-Arg-Pro-Ala-Val-$NH_2$

The above mentioned tetrapeptide was synthesized using solid phase synthesis via stepwise couplings. All the amino acids were protected at their α-amino group with a t-butyloxycarbonyl (BOC) group. Tosyl (TOS) was used to protect the side chain of Arg. The protected amino acids were used 2.5 equivalents in excess compared to each equivalent of substitution of the resin. All the couplings were done by DCC/HOBt and were at equal equivalents of the protected amino acids. All the amino acids were dissolved in $CH_2Cl_2$ except Arg which was dissolved in DMF.

The washing, deprotecting and coupling steps were as follows:

| | |
|---|---|
| 1. $CH_2Cl_2$ | 2 × 3 min |
| 2. 50 percent TFA - $CH_2Cl_2$ | 1 × 3 min |
| 3. 50 percent TFA - $CH_2Cl_2$ | 1 × 30 min |
| 4. $CH_2Cl_2$ | 1 × 3 min |
| 5. 40 percent isopropanol - $CH_2Cl_2$ | 2 × 3 min |
| 6. $CH_2Cl_2$ | 2 × 3 min |
| 7. 10 percent diisopropylethylamine | 2 × 10 min |
| 8. $CH_2Cl_2$ | 1 × 3 min |
| 9. amino acid | 1 × 3 min |
| 10. HOBt | 1 × 3 min |
| 11. DCC | 1 × 120 min |
| 12. $CH_2Cl_2$ | 2 × 3 min |
| 13. 40 percent isopropanol - $CH_2Cl_2$ | |
| 14. DMF | 1 × 3 min |
| 15. $CH_2Cl_2$ | 2 × 3 min | a. Synthesis

The protected peptide was synthesized using the Beckman Model 990 peptide synthesizer. The resulting tetrapeptide resin was 0.67 meg/g and the synthesis began with 5.0 g (3.35 mmol) of resin. The resulting tetrapeptide was then acetylated by treating the resin with:

| | |
|---|---|
| 1. $CH_2Cl_2$ | 2 × 3 min |
| 2. 50 percent TFA - $CH_2Cl_2$ | 1 × 3 min |
| 3. 50 percent TFA - $CH_2Cl_2$ | 1 × 30 min |
| 4. $CH_2Cl_2$ | 1 × 3 min |
| 5. 40 percent isopropanol - $CH_2Cl_2$ | 2 × 3 min |
| 6. $CH_2Cl_2$ | 2 × 3 min |
| 7. 10 percent diisopropylethylamine | 2 × 10 min |
| 8. $CH_2Cl_2$ | 1 × 3 min |
| 9. 50 percent acetic anhydride - $CH_2Cl_2$ with catalytic amount of DMAP | 1 × 120 min |
| 10. $CH_2Cl_2$ | 2 × 3 min |
| 11. 40 percent isopropanol - $CH_2Cl_2$ | 2 × 3 min |
| 12. DMF | 1 × 3 min |
| 13. $CH_2Cl_2$ | 2 × 3 min |

The peptide resin was dried under reduced pressure after washing with ethanol (2×50 ml).

b. HF Cleavage

The crude tetrapeptide was obtained by cleaving the resin-peptide with HF (25 ml) and anisole (25 ml) for 4 hours at 0° C. The HF was removed under reduced pressure. Diethyl ether (150 ml) was added to the mixture. The solution was stirred and transferred to a sintered glass funnel and washed with additional diethyl ether (3×100 ml). The peptide was extracted from the resin with 10 percent HOAc (3×100 ml) and the aqueous solution lyophilized to yield 1.20 g.

c. Purification

The product was purified by preparative high performance liquid chromatography (HPLC) with the following conditions: Whatman Column Partisil M20 10/50 ODS3; 300 mg sample using an isocratic 15 percent $CH_3CN/0.01M$ $NH_4OAc$ system (pH 5 adjusted with HOAc); flow rate of 15 ml/min; 220 nm detection wavelength. All the pure fractions were collected. The organic solvent was evaporated and the aqueous solution lyophilized to yield 258 mg of a white solid.

---

Amino Acid Analysis: Pro, 1.00; Ala, 1.00; Val, 1.00; Arg, 1.01; 83 percent peptide.
Thin layer chromatography (Silica 60/Analtech)
    $R_f(I)$ = 0.50 (Butanol:acetic acid:water/3:1:1)
    $R_f(II)$ = 0.59 (Butanol:pyridine:acetic acid:water/4:1:1:2)
    $R_S(III)$ = 0.29 (Butanol:acetic acid:water:ethyl acetate/1:1:1:1)

---

EXAMPLE 2

Synthesis of a Tetrapeptide:
Acetyl-Aro-Pro-Val-Ala-$NH_2$ a. Synthesis

The tetrapeptide was prepared on the Applied Biosystems 430A Peptide Synthesizer. The Std 1 cycle procedure (manufacturer's Version 1.40) was used which coupled each amino acid once except for BOC-Tos-Arg which was double coupled. The following prepacked starting materials were used in the synthesis:

| Reactant | Source | mmoles | Amount |
|---|---|---|---|
| p-Methyl-BHA-Resin | ABI | 0.50 | 760 mg |
| BOC—Tos—Arg | ABI | 2.0 | 857 mg |
| BOC—Pro | ABI | 2.0 | 430 mg |
| BOC—Val | ABI | 2.0 | 434 mg |
| BOC—Ala | ABI | 2.0 | 378 mg |

After the BOC group of arginine was removed and the peptide resin was neutralized and washed, the compound was acetylated using 10% acetic anhydride in $CH_2Cl_2$ (15 ml) in the presence of 4-dimethylaminopyridine (20 mg). After 60 minutes, the peptide was checked by the ninhydrin test to ensure complete acetylation. The peptide-resin was washed with $CH_2Cl_2$ (3×15 ml) and vacuum dried (room temperature) to yield 1.0 g of material.

b. HF Cleavage

The peptide was cleaved from the resin using 10 ml of HF in the presence of 1.5 ml of anisole. The mixture was stirred at 0° C. for 1.5 hours, after which the HF was removed under reduced pressure. The mixture was washed with $Et_2O$ (3×50 ml) and air dried. The peptide/resin mixture was extracted with 25% aqueous HOAc (3×50 ml).

c. Purification

The aqueous filtrate was lyophilized to yield 240 mg of crude material. This material was passed through an Amberlite IRA 68 (acetate form) ion exchange resin in water. Fractions containing peptide were combined and lyophilized (220 mg).

The peptide was purified on a Whatman Partisil 20M 10 ODS-3 (22 mm×50 cm) column using 15% acetonitrile (0.1% trifluoroacetic acid) and aqueous 0.1% trifluoroacetic acid as the eluting solvents (10.0 ml/min). The elution was monitored by HPLC and the appropriate fractions were combined and the solvent removed under reduced pressure. The residue was dissolved in $H_2O$ and lyophilized twice to give 167 mg of product for an overall yield of 50%.

---

Amino Acid Analysis: Arg, 1.04; Pro, 1.02; Val, 1.00; Ala, 1.01; 72 percent peptide.
Thin layer chromatography (Silica Gel GF 250 μm plates)
    $R_f(I)$ = 0.37 (n-BuOH:HOAc:$H_2O$/3:1:1)
    $R_f(II)$ = 0.15 ($CHCl_3$:MeOH:HOAc/60:35:5)
    $R_f(III)$ = 0.48 (n-BuOH:HOAc:$H_2O$:EtOAc/1:1:1:1)

---

EXAMPLE 3

Synthesis of a Tetrapeptide:
Acetyl-Aro-Pro-Asp-Val-$NH_2$ a. Synthesis

The title compound was synthesized by standard solid phase synthesis using an automatic Beckman Synthesizer Model 990. The synthesis was begun with 5.0 g of BHA resin (0.67 meg/g). After the coupling of BOC-Arg(Tos) was completed, the tert-butyloxycarbonyl protecting group was removed with 50 percent TFA in $CH_2Cl_2$ and the resin-peptide was acetylated with 50 percent acetic anhydride in $CH_2Cl_2$ in the presence of catalytic amount of DMAP. The peptide-resin was washed with ethanol (2×50 ml) and dried under reduced pressure overnight prior to the HF cleavage. The dry peptide-resin weighed 6.5 g.

b. HF Cleavage

The crude tetrapeptide was obtained by cleaving 6.5 g of the resin-peptide with HF (25 ml) and anisole (25 ml) at 0° C. for 4 h. The HF was evaporated under reduced pressure and diethyl ether (150 ml) was added to the reaction mixture. The crude peptide and resin were transferred to a sintered glass funnel and washed with diethyl ether (3×100 ml). The peptide was extracted with 10% HOAc (3×100 ml) and the aqueous solution lyophilized to yield 900 mg of white solid.

c. Purification

The crude product (98 percent pure by HPLC) was desalted on a Sephadex LH-20 column (100 g, 2.5 cm×89 cm) using 10 percent HOAc as eluant. After lyophilization the product was a white fluffy solid weighing 800 mg of white solid.

---

Amino Acid Analysis: Arg, 0.99; Val, 1.00; Pro, 1.05; Asp, 1.01.
Thin layer chromatography (Silica 60/Merck, 250 F)
    $R_f(I)$ = 0.51 (n-BuOH:HOAc:$H_2O$/3:1:1)
    $R_f(II)$ = 0.60 (n-BuOH:HOAc:$H_2O$:EtOAc/1:1:1:1)
    $R_f(III)$ = 0.59 (n-BuOH:Pyridine:HOAc:$H_2O$/4:1:1:2)

---

EXAMPLE 4

Synthesis of N-α-formyl-Arg-Pro-Asp-Val a. N-t-butyloxycarbonyl-β-benzyl-Aspartyl-Valine benzyl ester Into 80 ml $CH_2Cl_2$ was dissolved 3.23 g N-t-butyloxycarbonyl-β-benzyl-Asp and 3.97 g Val-benzyl ester p-tosylate. Diisopropylethylamine (1.74 ml) was added and the solution brought to 5°. To the mixture was added 2.06 g DCC. The mixture was stirred at 5° for 30 minutes then another two hours at ambient temperature. The precipitate was filtered and the filtrate extracted with water, 10 percent citric acid solution and saturated sodium bicarbonate solution. Solvent removal gave an oil which was purified by chromatography on silica gel 60 with 97:3 $CH_2Cl_2$-MeOH. The product, an oil, weighed 3.46 g.

b. N-t-butyloxycarbonyl-Prolyl-β-benzyl-Aspartyl-Valine benzyl ester

Deprotection of 3.41 g of the above product with 60 ml 2:1 $CH_2Cl_2$-TFA for 30 minutes gave the trifluoroacetate salt as an oil. The free amine was obtained by neutralization with saturated sodium carbonate solution and extraction into $CH_2Cl_2$. The extract was reduced in volume by evaporation then added to 1.05 g N-t-butyloxycarbonyl-Pro. A solution of 0.73 g HOBt in 2 ml DMF was added followed by 0.99 g DCC. The mixture was stirred 2½ hours then filtered. The filtrate was extracted with water, 10 percent citric acid solution and twice with saturated sodium bicarbonate solution. After drying, the solvent was removed leaving an oil. The product was purified by flash chromatography on silica gel 60 with 9:1 $CH_2Cl_2$-$CH_3CN$. The fraction containing the major component yielded 2.31 g colorless oil. IR spectrum: 1740 $cm^{-1}$, 1695 $cm^{-1}$, and 1675 $cm^{-1}$.

c. N-α-formyl-N$^g$-nitro-Arginyl-Prolyl-β-benzyl-Aspartyl-Valine benzyl ester

To 2.23 g of the above product was added 60 ml 1:2 TFA-$CH_2Cl_2$. The solution was stirred 30 minutes, then the solvent removed under reduced pressure leaving a waxy solid which was washed with petroleum ether. Into 15 ml DMF was dissolved 0.72 g N-α-formyl-N$^g$-nitro-Arginine and 0.33 ml N-methylmorpholine. The solution was chilled to −20° and 0.40 g isobutylchloroformate was added dropwise. The mixture was stirred at −20° to −10° for 20 minutes then a chilled solution of the prolyl-β-benzyl-aspartyl-valine benzyl ester trifluoroacetate in 20 ml DMF and 0.33 ml N-methyl-morpholine was added. The mixture was stirred at −15° for 20 minutes then the cooling bath removed and stirring continued at ambient temperature for two hours. Most of the solvent was removed under reduced pressure. The residue was dissolved in 50 ml $CH_2Cl_2$ and extracted with water, 10 percent citric acid solution and saturated sodium bicarbonate solution. The organic layer was dried and the solvent evaporated yielding 2.08 g.

Thin layer chromatography (silica gel GF):
$R_f(I) = 0.56$ ($CH_2Cl_2$:MeOH/9:1)
$R_f(II) = 0.72$ ($CHCl_3$:MeOH:HOAc/8:1:1)

d. N-α-formyl-Arginyl-Prolyl-Aspartyl-Valine

Deprotection was accomplished by transfer hydrogenation with 30 ml 5 percent formic acid-ammonium formate over palladium black. The reaction mixture was stirred in a balloon-stoppered flask for 18 hours. After filtering the mixture through Celite, the solvent was removed under reduced pressure. The residue was dissolved in water and lyophilized. The product was purified on a 1.6×60 cm column of DEAE-Sephadex. Elution was begun with 0.02M ammonium bicarbonate pH 8.5, collecting 150 drop fractions. After 52 fractions had been collected, a gradient of 0.02 to 0.20M ammonium bicarbonate over 2 L was begun. The largest peak in the chromatogram eluted centered at fraction 88. Fractions 75–100 were combined and lyophilized yielding a fluffy amorphous solid. HPLC: rt=9.4 min with 10 percent MeOH−0.01N $NH_4OAc$ pH 5 at 1.5 ml/min on Bondapak-$C_{18}$.

Thin layer chromatography, (silica gel 60):
$R_f(I) = 0.16$ (n-BuOH:HOAc:$H_2O$/3:1:1)
$R_f(II) = 0.27$ (n-BuOH:HOAc:$H_2O$:pyr/15:3:12:10)
$R_f(III) = 0.42$ (EtOAc:pyr:HOAc:$H_2O$/5:5:1:3)
Amino acid analysis: Asp, 0.99; Pro, 0.97; Val, 1.05; Arg, 1.00; 38 percent peptide.

EXAMPLE 5

Synthesis of a Tetrapeptide:
Acetyl-Arg-Pro-Val-Ala-NH($CH_3$)

a. Synthesis

The tetrapeptide was prepared on the Applied Biosystems 430A Peptide Synthesizer. The Std 1 cycle procedure Version 1.40 was used which coupled each amino acid once except for BOC-Tos-Arg which was double coupled. The following starting materials were used in the synthesis:

| Reactant | Source | mmoles | Amount |
|---|---|---|---|
| Methylamine-PAM-Resin | 122-12-1R | 0.5 | 1.0 g |
| BOC—Tos—Arg | ABI | 2.0 | 857 mg |
| BOC—Pro | ABI | 2.0 | 430 mg |
| BOC—Val | ABI | 2.0 | 434 mg |
| BOC—Ala | ABI | 2.0 | 378 mg |

After the BOC group of arginine was removed and the peptide resin was neutralized and washed, the compound was acetylated using 10% acetic anhydride in $CH_2Cl_2$ (10 ml) with 4-dimethylaminopyridine (15 mg). The peptide-resin was washed with DMF (3 * 10 ml) followed by $CH_2Cl_2$ (3 * 10 ml) and vacuum dried to yield 1.6 g of material.

b. HF Cleavage

The peptide was cleaved from the resin using 30 ml of HF in the presence of anisole (1.5 ml). The mixture was stirred at 0° C. for 1 hour and 4 hours at 23°, after which the HF was removed under reduced pressure. The mixture was washed with Et2O (3 * 50 ml) and air dried. The peptide was extracted from the resin with 20% aqueous acetic acid (3 * 50 ml).

c. Purification

The aqueous extract was lyophilized to give a crude solid. This material was passed through an Amberlite IRA 68 (acetate form) ion exchange resin in water. Fractions containing peptide were combined and lyophilized.

The peptide was purified on a Vydac 218TP5022 C-18 reverse phase prep column using a 0% to 3.75% acetonitrile in aqueous 0.1% trifluoroacetic acid gradient during 120 min. at 14 ml/min. The elution was monitored by HPLC and the appropriate fractions were combined and the solvent removed at reduced pressure. The residue was dissolved in water (10 ml) and lyophilized to yield 218 mg of pure product.

Amino Acid Analysis: Arg, 1.00; Pro, 0.98; Val, 0.99; Ala, 1.02; 68 percent peptide.
Thin layer chromatography (Merck silica gel plates)

-continued $R_f(I) = 0.31$ (n-BuOH:HOAc:H$_2$O/4:1:1)
$R_f(II) = 0.41$ (n-BuOH:HOAc:EtOAC:H$_2$O/1:1:1:1)
$R_f(III) = 0.71$ (n-BuOH:Pyr:HOAc:H$_2$O/5:4:4:2)

EXAMPLE 6

Synthesis of a Pentapeptide Arg-Pro-Ala-Val-Tyr

The peptide was synthesized by the solid phase method, starting with BOC-(BZLCl$_2$)-Tyr resin ester (4.4 g, 0.40 meg/g). The resin was coupled sequentially with three equivalents each of BOC-Val, BOC-Ala, BOC-Pro, and CBZ$_3$-Arg. DCC and HOBt in 4:1 CH$_2$Cl$_2$:DMF were the coupling agents. The resin was cleaved with HF (40 ml) in anisole (5 ml) for 45 minutes at 0°. The solid residue was extracted with 10 HOAc, filtered and the aqueous solution lyophilized to give 1.56 of the crude peptide.

Purification was via Sephadex SPC 25 chromatography (2.6×90 cm column) eluting with a stepwise gradient of NH$_4$OAc: 0.05 M, pH 5 (2 l), 0.15 M, pH 5 (1 l), 0.15 M, pH 6.7 (2 l); 100 ml/hr flow rate, 12.5 ml fractions, 280 nm detection. Isolation of fractions 198–207 gave the title peptide as a colorless solid, 1.13 g.

Thin layer chromatography, (silica gel G, 250):
$R_f(I) = 0.24$ (n-PrOH:NH$_4$OH/84:37)
$R_f(II) = 0.64$ (Trifluoroethanol:NH$_4$OH/78:22)
$R_f(III) = 0.58$ (n-BuOH:HOAc:H$_2$O:pyr/15:3:12:10)
Amino Acid Analysis: Arg, 1.00; Ala, 0.96; Pro, 0.97; Val, 1.03; Tyr, 1.01; 67 percent peptide.

EXAMPLE 7

Biological Activity: Cyclic GMP Assay

This assay measures the ability of a peptide of this invention to bind to the cell membrane receptor of the intact MOLT-4 cell and selectively stimulate production of cyclic GMP, as does human thysplenin and human thymopentin.

The MOLT-4 cell line was obtained from the American Type Culture Collection of Rockville, Md. MOLT-4 cells were freshly seeded and grown for 3 days with harvesting as described in T. Audhya et al, *Arch. Biochem Biophys.*, 234: 167–177 (1984). The cells were washed 3 times in PBS and resuspended in RPMI 1640 at a concentration of $1.0 \times 10^7$ cells/ml and were allowed to equilibrate at 37° C. for 30 minutes before the addition of the test tetrapeptides and pentapeptides (25 ul) and control peptides. The incubation was allowed to proceed in a shaking water bath for 4–5 minutes and was then terminated by addition of 1 ml ice-cold TCA (10 percent).

The cells in TCA were homogenized and sonicated to release cyclic nucleotide. The suspension was centrifuged at 3000×g for 20 minutes at 4° C. The resulting precipitate was dissolved in 0.1N NaOH to determine the protein content. TCA was removed from the supernatant fraction by extracting 4 times with 5 ml of water-saturated diethyl ether. After the final extraction, the remaining traces of ether were removed by heating for 10 minutes in a 50° C. water bath. After lyophilization the sample was reconstituted in 50 mM acetate buffer (pH 6.2) for radioimmunoassay of cyclic GMP.

Figure 1:
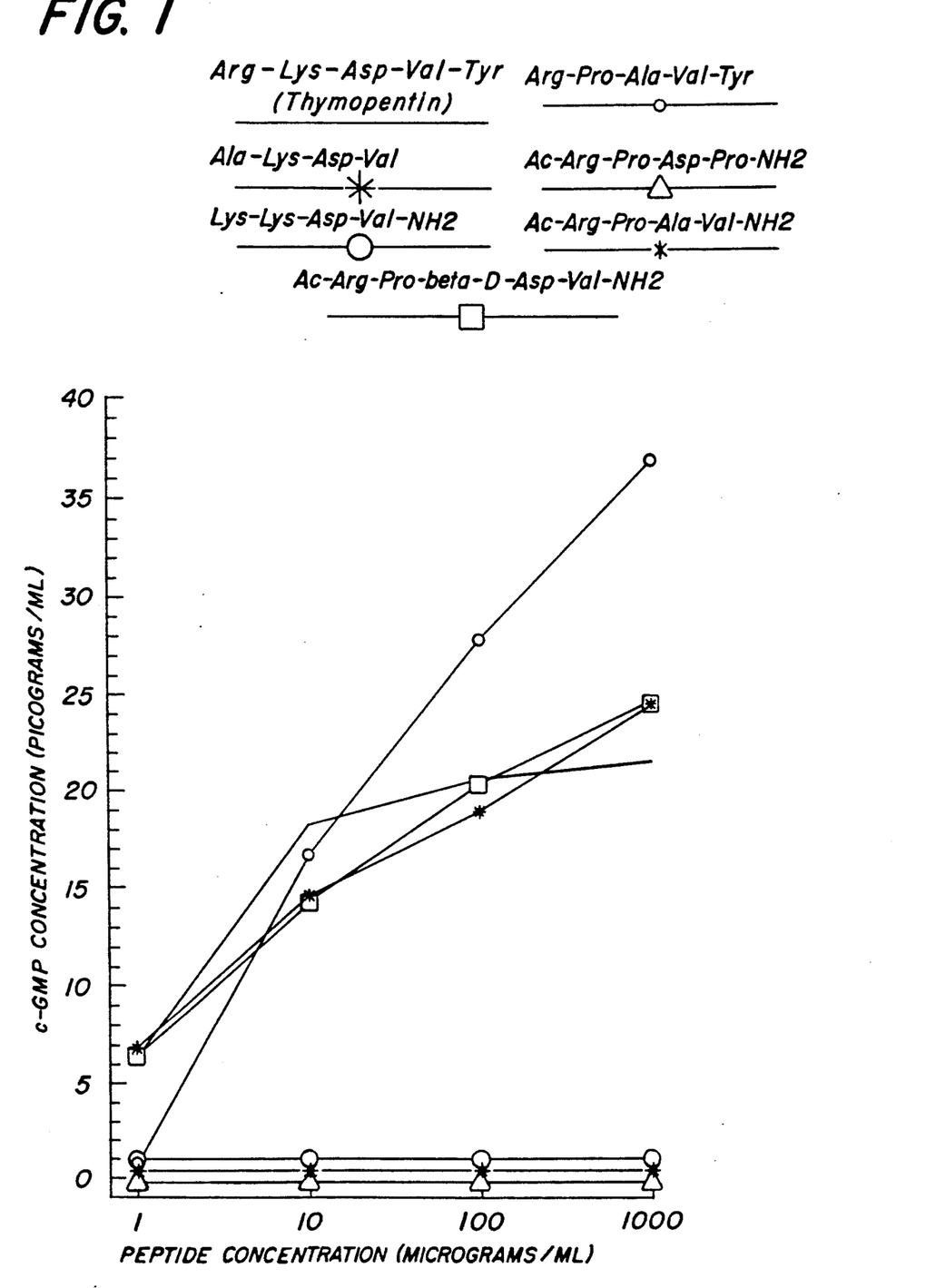
FIG. 1 is a graphical illustration of a MOLT-4 cGMP assay plotting peptide concentration (μg/ml) against cGMP levels (picogram/ml) and comparing the activity therein of thymopentin (TP-5) and peptides of this invention against controls.
Figure 2:
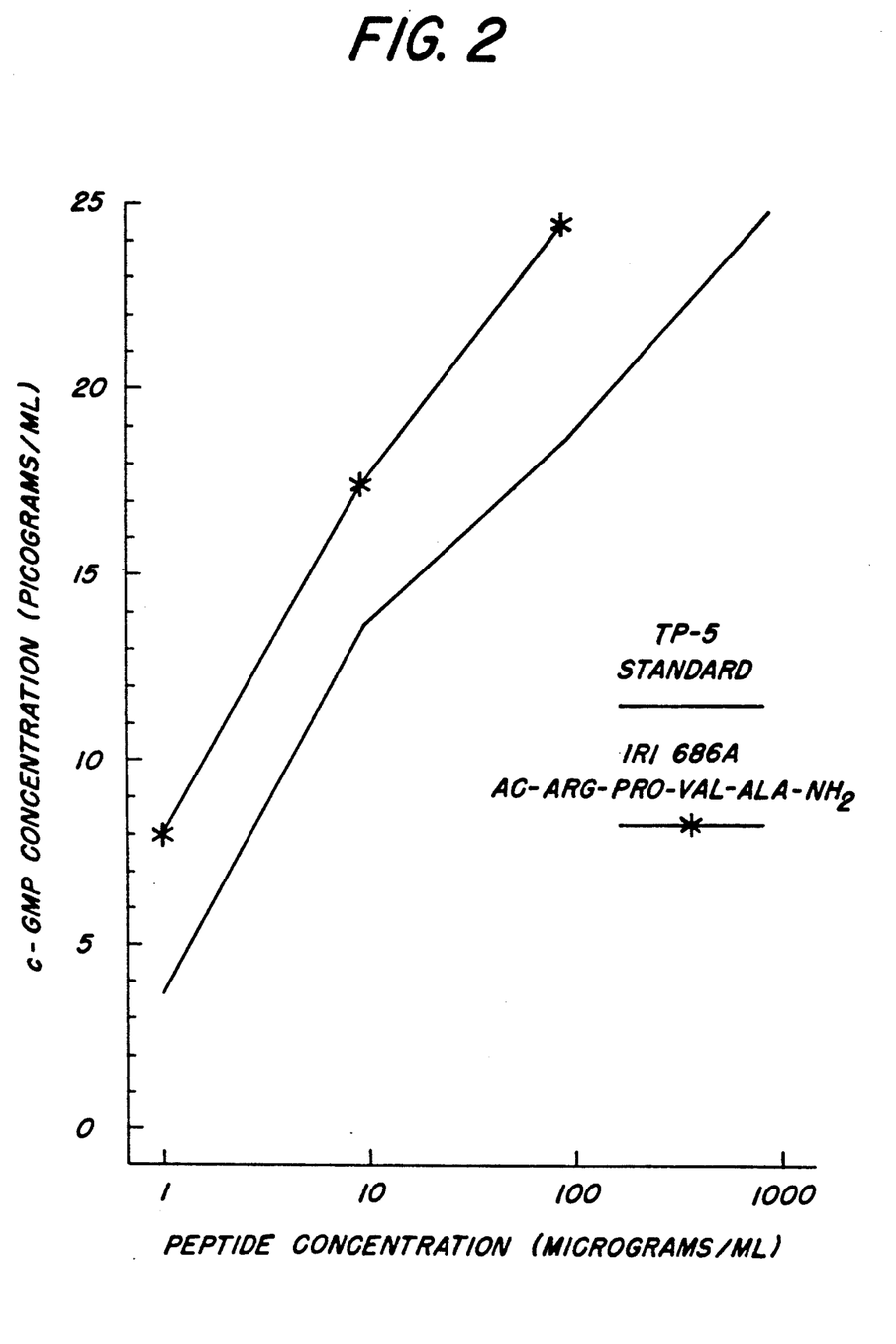
FIG. 2 is a graphical illustration of a MOLT-4 cGMP assay plotting peptide concentration (μg/ml) against cGMP levels (picogram/ml) and comparing the activity therein of thymopentin (TP-5) and a peptide Ac-Arg-Pro-Val-Ala-$NH_2$ of this invention

FIG. 1 shows typical dose-response curves evaluated from 1 to 1000 μgs/ml for active peptides Acetyl-Arg-Pro-β-D-Asp-Val-NH$_2$, Arg-Pro-Ala-Val-Tyr and Acetyl-Arg-Pro-Ala-Val-NH$_2$ compared with thymopentin and inactive peptides Acetyl-Arg-Pro-Asp-Pro-NH$_2$, Ala-Lys-Asp-Val, and Lys-Lys-Asp-Val-NH$_2$ in MOLT-4 cells. FIG. 2 shows dose response curves evaluated from 1 to 100 μgs/ml for active peptide Acetyl-Arg-Pro-Val-Ala-NH$_2$ compared to the thymopentin standard in MOLT-4 cells.

A threshold activity was determined for each peptide tested. This is defined as the lowest concentration of the test peptide which induced an intracellular level of cyclic GMP greater than two standard deviations above the control. The controls had intracellular cyclic GMP values of less than 0.5 picomoles/ml (mean±standard deviation). Test results were considered positive if the level of cyclic GMP was greater than 2 times (2 standard deviations) that determined for the parallel negative control.

Results of the cyclic GMP assays are shown in FIG. 1 and its corresponding Table I and in FIG. 2 and its corresponding Table II in which representative peptides of the invention have been assayed in comparison with thymopentin and control peptides. These results were compared to thymopentin (Arg-Lys-Asp-Val-Tyr) on MOLT-4 because the human thysplenin pentapeptide "SP-5" (Arg-Lys-Ala-Val-Tyr) is inactive on MOLT-4. These results demonstrate the biological activity of the peptides of the invention in stimulating T cell helper activity in MOLT-4 cells.

TABLE I

| cGMP Concentration (picograms/ml) | | | | |
|---|---|---|---|---|
| Peptide concentration (μg/ml): | 1 | 10 | 100 | 1000 |
| Arg—Lys—Asp—Val—Tyr | 6.4 | 18.3 | 20.8 | 21.9 |
| Arg—Pro—Asp—Val—NH$_2$ | 0.1 | 17.1 | 19.3 | 24.8 |
| Acetyl-Arg—Pro—Asp—Val—NH$_2$ | 4.55 | 8.99 | 19.62 | 24.09 |
| Acetyl-Arg—Pro—Glu—Val—NH$_2$ | 4.7 | 9.41 | 16.76 | 25.00 |
| Acetyl-Arg—Pro—Ala—Val—NH$_2$ | 7.1 | 14.6 | 19.1 | 24.5 |
| Acetyl-Arg—Aib—Glu—Val—NH$_2$ | 3.7 | 11.0 | 17.7 | 24.9 |
| Acetyl-Arg—Pro—Gln—Val—NH$_2$ | 18.75 | 29.68 | 34.98 | 40.23 |
| Acetyl-Arg—Pro—Glu—Val | 4.1 | 11.9 | 7.9 | 30.8 |
| Acetyl-Arg—Aib—Ala—Val—NH$_2$ | 18.78 | 30.45 | 36.17 | 39.48 |
| Acetyl-Arg—Pro-β-D-Asp—Val—NH$_2$ | 6.6 | 14.3 | 20.5 | 25.0 |
| Acetyl-Arg—Pro-β-Asp—Gly—NH$_2$ | 20.56 | 31.83 | 36.66 | 34.95 |
| Lys—Lys—Asp—Val—NH$_2$ | 0.33 | 0.31 | 0.34 | 0.33 |
| Lys—Arg—Asp—Val | 0.44 | 0.43 | 0.44 | 0.39 |
| Arg—Gly—Asp—Ser | 0.71 | 0.50 | 0.68 | 0.58 |
| Arg—Pro—Ala—Val—Tyr | 0.09 | 16.41 | 27.90 | 37.14 |
| Arg—Pro—Ala—Val—Tyr—NH$_2$ | 3.71 | 14.15 | 12.83 | 12.57 |
| Acetyl-Arg—Lys—Ala—Val—Tyr—NH$_2$ | 3.00 | 8.86 | 12.83 | 18.43 |
| Acetyl-Arg—Pro—Val—Ala—NH(CH$_3$) | 4.00 | 9.00 | 16.00 | |
| Acetyl-Arg—Pro—Asp—Val—NH(CH$_3$) | 6.00 | 9.00 | 19.80 | |

0 peptide control varies from 0–0.3 pg/ml.

TABLE II

| cGMP Concentration (picograms/ml) | | | | |
|---|---|---|---|---|
| Peptide concentration (μg/ml): | 1 | 10 | 100 | 1000 |
| Arg—Lys—Asp—Val—Tyr | 3.55 | 13.56 | 18.70 | 24.85 |
| Acetyl-Arg—Pro—Val—Ala—NH$_2$ | 7.77 | 17.39 | 24.47 | — |
| Acetyl-Arg—Pro—Val—Ala—NH(CH$_3$) | | | | |

Note:
Background is 0.19 picomoles cGMP/ml.

EXAMPLE 8

Enzymatic Stability

To illustrate the stability of a peptide of the present invention against degradation by intestinal and serum enzymes, an exemplary peptide Acetyl-Arg-Pro-Asp-Val-NH$_2$ was incubated at 37° C. in rat intestinal juice and human serum for up to 120 minutes. Similarly treated for comparison were the tetrapeptide Arg-Lys-Asp-Val and thymopentin. HPLC revealed that Arg-Lys-Asp-Val was totally digested after 25 seconds. Thymopentin was 50% degraded at about 20 seconds. The peptide of this invention remained substantially undegraded in both serum and intestinal juice for at least 120 seconds.

EXAMPLE 9

Biological Activity: Tumor Inhibition Assay

An assay is performed using normal healthy C3H laboratory mice. The mice, in groups of 12 to 20, are injected subcutaneously with either 30 ng or 30 μg of a peptide of the present invention once per week. This peptide (acetyl-Arg-Pro-Val-Ala-NH$_2$) called splenoralin was administered in citrate buffer containing 1% glycine and 2% D-raffinose pentahydrate, as described in pending United States patent application Ser. No. 336,236, incorporated herein by reference. A control group of mice were injected similarly with 30 μg of the glycine-raffinose vehicle without the peptide.

Four weeks after the initiation of these weekly injections, each mouse was inoculated intradermally with $5 \times 10^6$ BP8 murine tumor cells. BP8 is a conventional benzpyrene induced murine tumor. Once every week thereafter, each mouse is injected with the same amount of either the peptide formulation or the vehicle alone.

Figure 3:
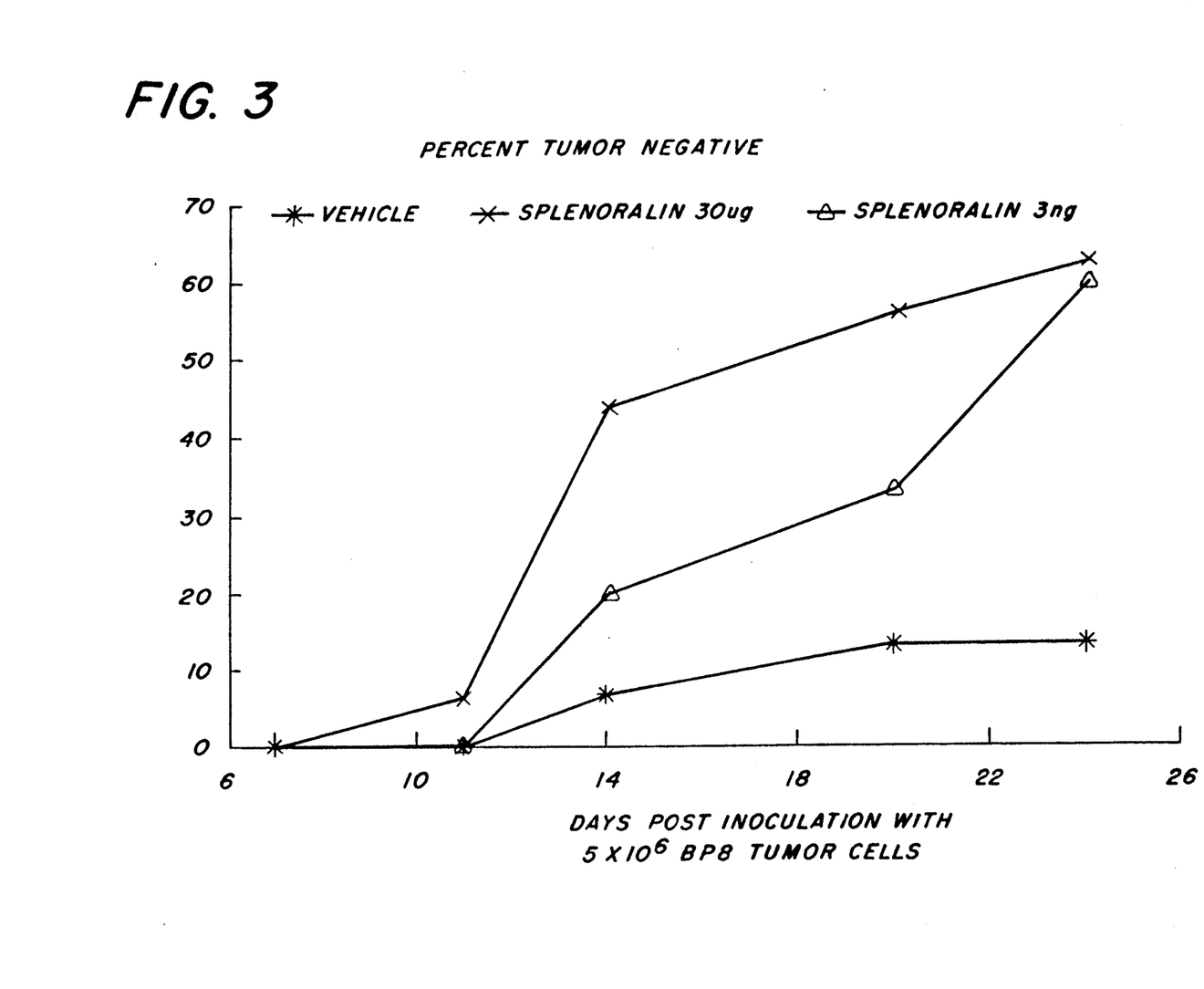
FIG. 3 is a graphical illustration of a BP8 tumor growth assay showing the inhibition of tumor growth in animals treated with a peptide of this invention versus a control. The graph plots the percentage of animals tumor negative vs the days post inoculation with tumor cells.
Figure 4:
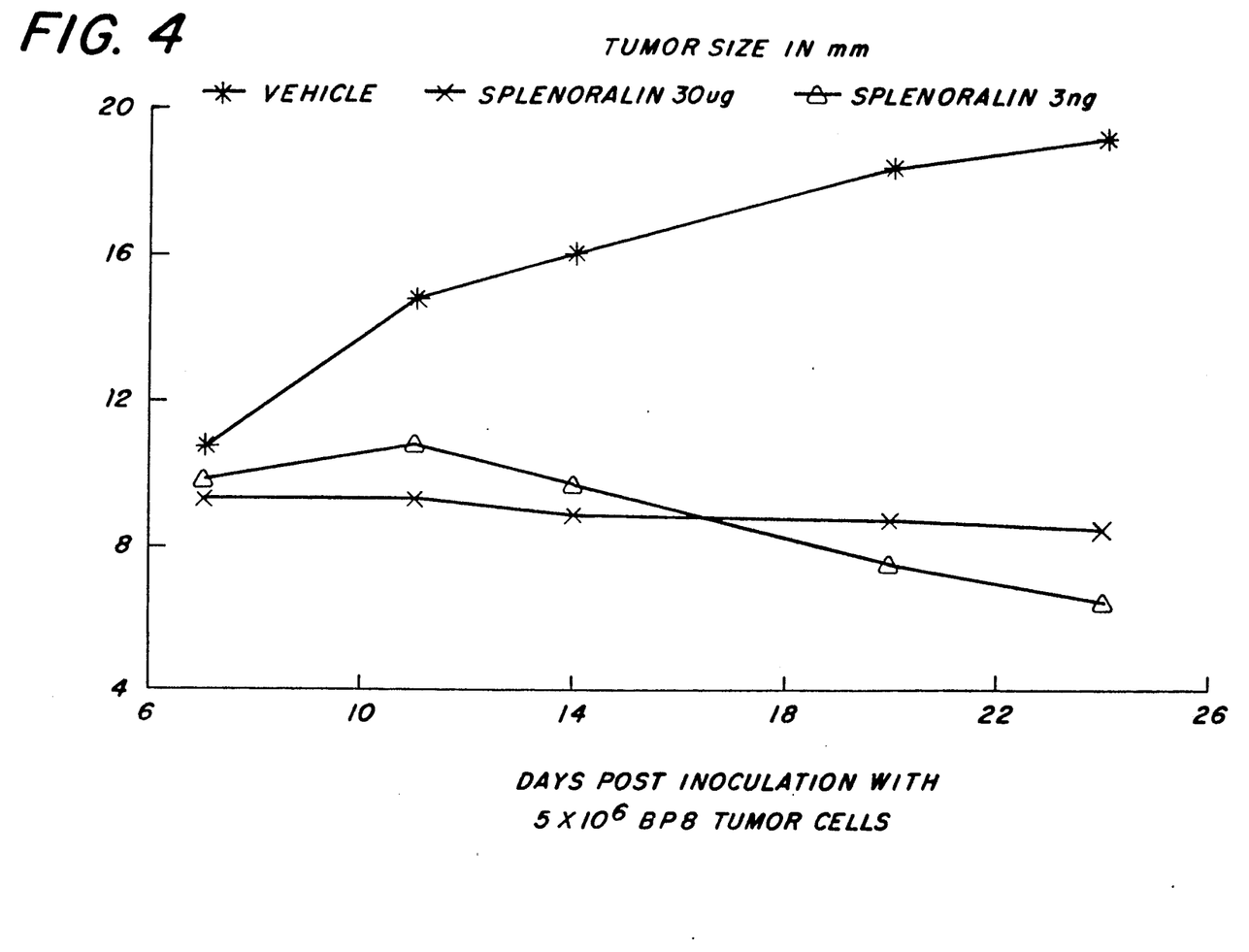
FIG. 4 is another graphical illustration of the BP8 assay plotting tumor size in millimeters vs. days post inoculation.

FIG. 3 indicates the percent of mice in each group which are negative for the presence of BP8 tumors in the days after the inoculation of tumor cells. FIG. 4 indicates for the same experiment the maximum size of tumors in those mice that did develop tumors.

The results of this experiment indicate that the administration of a peptide of this invention enabled the mice to resist the spread and growth of the tumor cells. The placebo treated mice are shown to have developed BP8 tumors. Thus the peptide appears to be activating the immune system of the animal to inhibit tumor growth, thus indicating enhancement of T cell helper activity.

EXAMPLE 10

Biological Activity: Viral Inhibition Assay

An assay is performed using normal healthy outbred CD1 laboratory mice. The mice, in groups of 30, are first injected subcutaneously with an LD50 lethal dose of murine-adapted influenza A/HK/68 virus. Starting 2 days after infection, each mouse was administered 0.03 μg of a peptide of the present invention subcutaneously. This peptide (acetyl-Arg-Pro-Val-Ala-NH$_2$) called splenoralin was administered in the formulation described above containing glycine and raffinose. A control group of mice were injected similarly with 0.03 μg of the glycine-raffinose vehicle without the peptide.

Each mouse was administered the same dosage of either the peptide or the vehicle alone five times a week.

Figure 5:
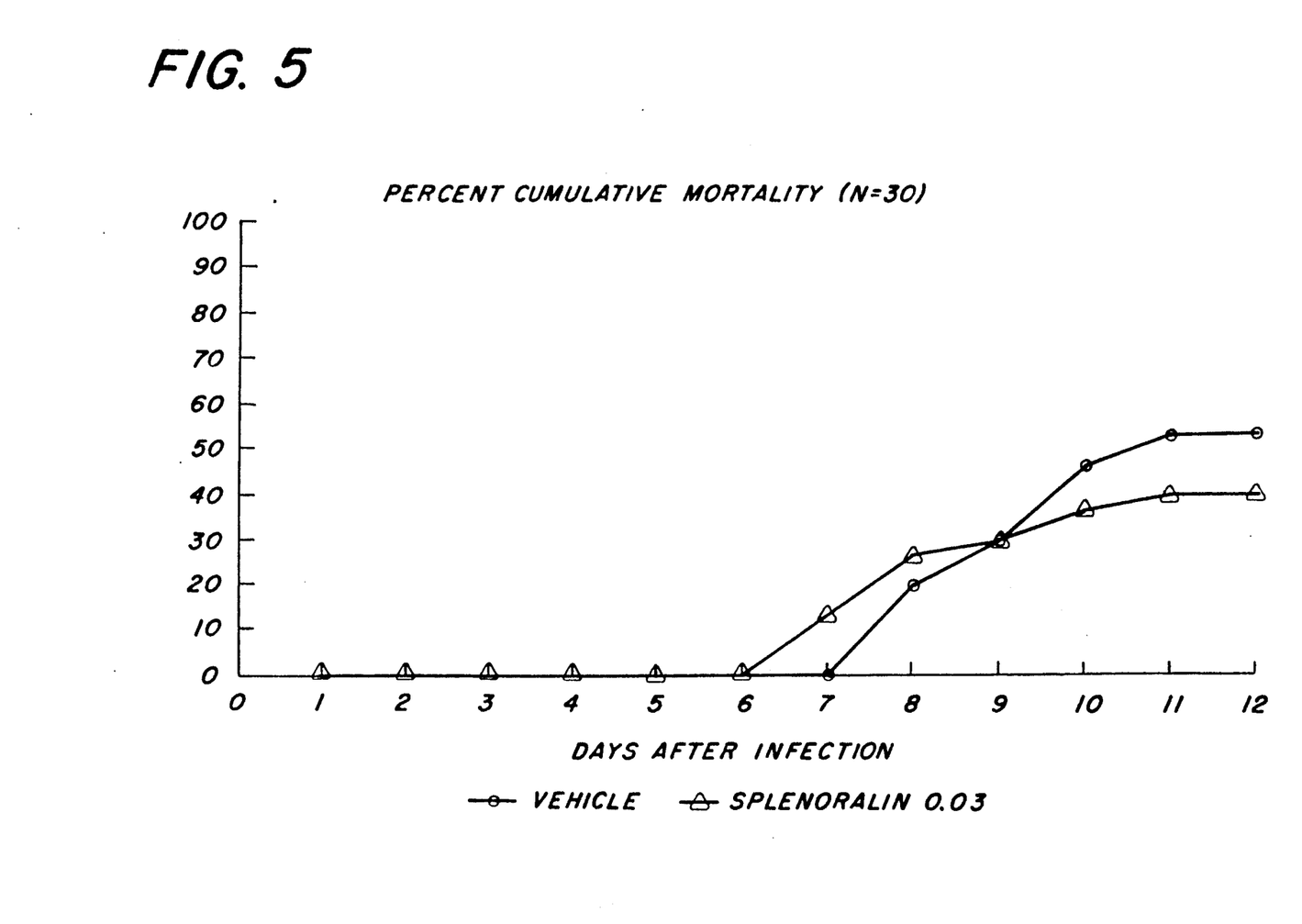
FIG. 5 is a graphical illustration of an influenza assay plotting percent cumulative animal mortality of 30 treated animals vs. days after infection of animals treated with a peptide of this invention vs. a control.

The results of this assay are indicated in FIG. 5, which plots the percent cumulative mortality against the days after viral infection. The graph shows that those mice treated with the peptide of this invention had a lower death rate over 12 days then did the placebo treated mice. Thus the peptide was exerting a therapeutic or enhancing effect on the immune system of the treated mice, enabling a greater number of mice to resist the viral infection.

EXAMPLE 11

Biological Activity: Diabetic Mice Assay

A strain of non-obese diabetic (NOD) laboratory mice maintained in Hopital Necker, Paris, France, have been bred in which the females spontaneously develop autoimmune disease of the pancreas. In the normal course of this disease in mice, the pancreatic cells are destroyed, resulting in loss of insulin production and diabetes mellitus. This mouse strain thus is a close model of Type I onset juvenile diabetes, which is normally treated with insulin replacement, but which can be typically slowed by immunosuppressive drugs, e.g., cyclosporin.

In this assay, groups of 12 to 20 NOD female mice are injected with 1 mg/kg body weight of a peptide of the present invention one time a week at weaning. This peptide (acetyl-Arg-Pro-Val-Ala-NH$_2$) called splenoralin was administered the above-described formulation containing glycine and raffinose. A control group of mice were injected similarly with 1 mg of the glycine-raffinose vehicle without the peptide one time a week.

Figure 6:
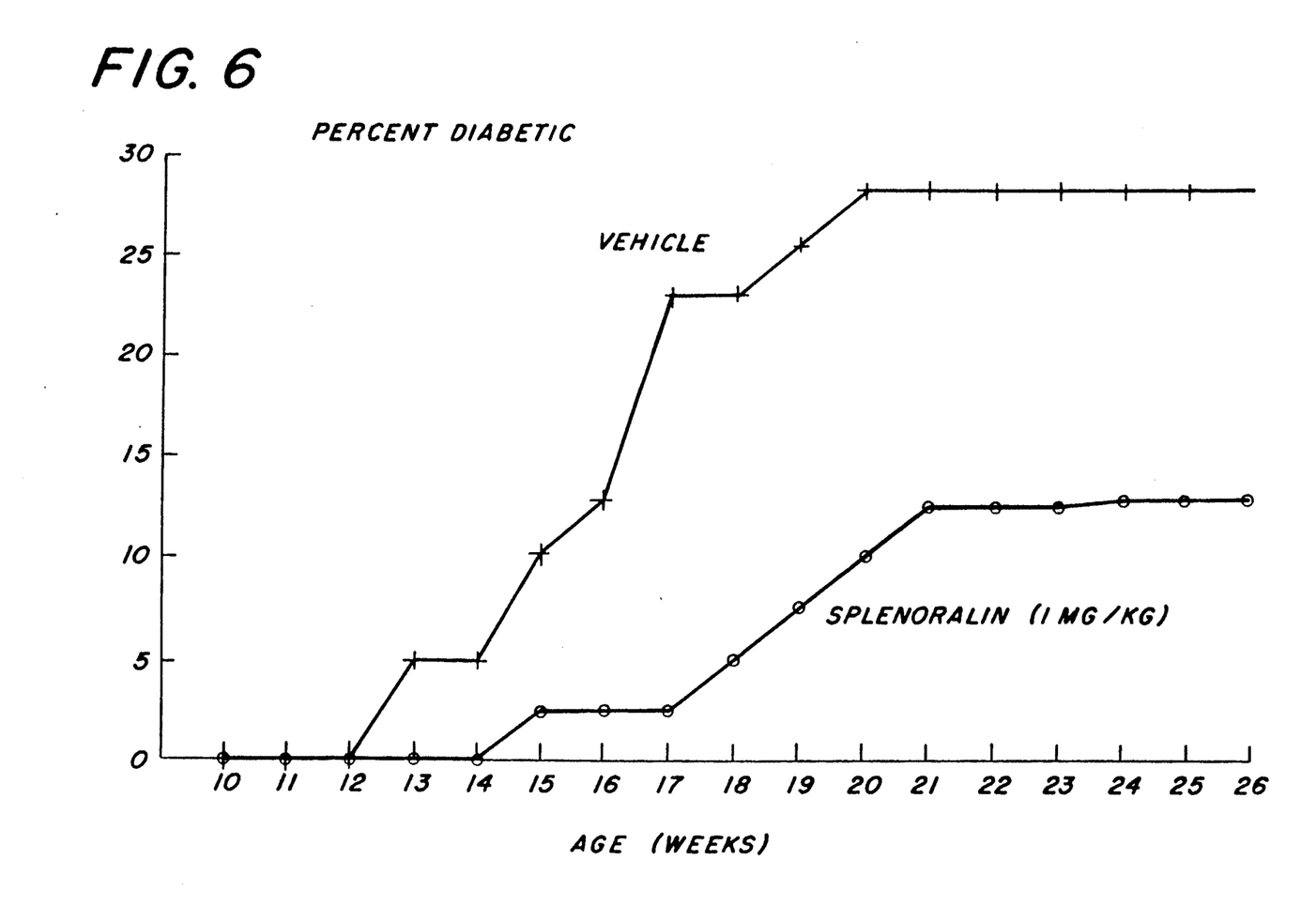
FIG. 6 is a graphical illustration of an assay indicating the occurrence of diabetes in a strain of diabetic mice treated with either a peptide of this invention or a control. Percent incidence of diabetes is plotted against the age in weeks of the mice.

FIG. 6 demonstrates the results of this therapy by plotting the incidence of diabetes (by percentage) vs. the age in weeks of the mice in this study. Surprisingly, treatment with a peptide of this invention restored the immune function and allowed survival of a greater number of animals than did the placebo, indicating a positive effect, e.g., stimulation or repair, on the deficient suppressor T cell function of these animals.

The above examples have been presented for illustrative purposes only and not to limit the scope of the present invention as set out in the following claims.

We claim:

1. A tetrapeptide having the formula or a pharmaceutically acceptable acid or base addition salt thereof, wherein R is H, lower alkyl, acetyl, formyl, lower alkanoyl;

X is Pro, dehydro-Pro, hydroxyl-Pro, D-Lys, Aib or Lys;

Y is a D or L form of an amino acid selected from Ala, Asp, Glu, Gln, Asn, beta-Asp, Val or Ile;

Z is Gly or a D or L form of an amino acid selected from Val, Ala, Leu or Ile;

$R^1$ is $NR^2R^3$, wherein $R^2$ or $R^3$ are H or a straight chain or branched alkyl or alkenyl having 1 to 6 carbon atoms, optionally substituted with an aryl group or aryl substituted with either a halogen or a straight chain or branched alkyl or alkenyl having 1 to 6 carbon atoms or wherein $R^2$ or $R^3$ together comprise a cyclic methylene group of 3 to 7 carbon atoms, provided that when X is Lys, and Z is Val, Y is other than Asp, Asn, Ala or Glu, and when X is Lys, Y is other than Asp.

2. The tetrapeptide according to claim 1 wherein X is Pro, Y is Asp, Ala, Glu, D-beta Asp, Val, Leu, or Ile and Z is Val or Ala.

3. The tetrapeptide according to claim 1 wherein R is acetyl, X is Pro or AIB.

4. The tetrapeptide according to claim 1 wherein $R^1$ is $NR^2R^3$, wherein only one of $R^2$ and $R^3$ may be H.

5. A tetrapeptide selected from the group consisting of

Arg-Pro-Asp-Val

Arg-Pro-Asp-Val-NH$_2$
Formyl-Arg-Pro-Asp-Val
Acetyl-Arg-Pro-Asp-Val
Acetyl-Arg-Pro-Asp-Val-NH$_2$
Acetyl-Arg-Pro-Asp-Val-NH(CH$_3$)
Acetyl-Arg-Pro-Asp-Ala-Val-NH$_2$
Acetyl-Arg-Pro-D-beta Asp-Val-NH$_2$
Acetyl-Arg-Pro-Glu-Val-NH$_2$
Acetyl-Arg-Pro-Glu-Val
Acetyl-Arg-Aib-Glu-Val-NH$_2$
Acetyl-Arg-Aib-Ala-Val-NH$_2$ or
Acetyl-Arg-Pro-beta-Asp-Gly-NH$_2$.

6. A peptide Acetyl-Arg-Pro-Val-Ala-NH$_2$.
7. A peptide Acetyl-Arg-Pro-Val-Ala-NH(CH$_3$).
8. A peptide Acetyl-Arg-Pro-Glu-Val-NH$_2$.
9. A peptide Acetyl-Arg-Pro-Glu-Val-NH(CH$_3$).
10. A peptide Acetyl-Arg-Pro-Asp-Val-NH(CH$_3$).
11. A pentapeptide having the formula or a pharmaceutically acceptable acid or base addition salt thereof, wherein $R^4$ is H, lower alkyl, acetyl, formyl, lower alkanoyl or des-amino;

X' is Pro, dehydro-Pro, hydroxy-Pro, D-Lys, Aib, or Lys;

Y' is a D or L form of an amino acid selected from Val, Ile, Leu, Ala, Asp, Glu, Gln, Lys;

Z' is a D or L form of an amino acid selected from Tyr, Val, Leu, His, Ala, Phe or Trp;

$R^5$ is OH or $NR^6R^7$, wherein $R^6$ and $R^7$ are H or a straight chain or branched alkyl or alkenyl having 1 to 6 carbon atoms, optionally substituted with an aryl group or aryl substituted with either a halogen or a straight chain or branched alkyl or alkenyl having 1 to 6 carbon atoms or wherein $R^4$ and $R^5$ together comprise a cyclic methylene group of 3 to 7 carbon atoms.

12. The pentapeptide according to claim 11 wherein X' is Pro or AIB.
13. The pentapeptide according to claim 12 wherein Y' is Val.
14. The pentapeptide according to claim 12 wherein Z is Tyr or Phe.
15. The pentapeptide according to claim 11 wherein R is acetyl, X is Pro or AIB, Y' is Val and Z is Tyr or Phe.
16. The pentapeptide according to claim 11 wherein $R^5$ is OH or $NR^6R^7$, wherein only one of $R^6$ and $R^7$ may be H.
17. A peptide Arg-Pro-Ala-Val-Tyr.
18. A peptide Arg-Pro-Ala-Val-Tyr-NH$_2$.
19. A peptide Acetyl-Arg-Lys-Ala-Val-Tyr-NH$_2$.
20. A pharmaceutical composition comprising a therapeutically effective amount of at least one tetrapeptide of claim 1 in a pharmaceutically acceptable formulation.
21. The composition according claim 20 to wherein said tetrapeptide is Acetyl-Arg-Pro-Val-Ala-NH$_2$.
22. The composition according to claim 20 wherein said tetrapeptide is Acetyl-Arg-Pro-Val-Ala-NH(CH$_3$).
23. The composition according to claim 22 wherein said tetrapeptide is Acetyl-Arg-Pro-Glu-Val-NH$_2$.
24. The composition according to claim 22 wherein said tetrapeptide is Acetyl-Arg-Pro-Glu-Val-NH(CH$_3$).
25. The composition according to claim 22 wherein said tetrapeptide is Acetyl-Arg-Pro-Asp-Val-NH(CH$_3$).
26. A pharmaceutical composition comprising a therapeutically effective amount of at least one pentapeptide of claim 12 in a pharmaceutically acceptable formulation.
27. The composition according to claim 20 which is suitable for oral administration.
28. The composition according to claim 26 which is suitable for oral administration.
29. A tetrapeptide according to claim 1 comprising Acetyl-Arg-Pro-D-Val-Ala-NH$_2$.
30. A tetrapeptide according to claim 1 comprising Acetyl-Arg-Pro-Val-D-Ala-NH$_2$.

* * * * *